United States Patent
Sanfilippo et al.

(10) Patent No.: US 7,595,427 B2
(45) Date of Patent: Sep. 29, 2009

(54) PROCESS FOR PRODUCTION OF STYRENE BY CATALYTIC GAS PHASE DEHYDROGENATION OF ETHYLBENZENE

(75) Inventors: Domenico Sanfilippo, Paullo (IT); Ivano Miracca, Milan (IT); Guido Capone, San Donato Milanese (IT); Vincenzino Fantinuoli, Porto Garibaldi (IT)

(73) Assignee: Snamprogetti S.p.A., San Donato Milanese (IT)

( * ) Notice: Subject to any disclaimer, the term of this patent is extended or adjusted under 35 U.S.C. 154(b) by 466 days.

(21) Appl. No.: 10/846,527

(22) Filed: May 17, 2004

(65) Prior Publication Data
US 2005/0177016 A1    Aug. 11, 2005

(30) Foreign Application Priority Data
Feb. 9, 2004  (IT) ................... MI2004A0198

(51) Int. Cl.
*C07C 2/64* (2006.01)
*B01J 8/18* (2006.01)

(52) U.S. Cl. ................ 585/444; 585/315; 585/316; 585/323; 585/403; 585/441; 585/445; 585/600; 585/661; 502/243; 422/139; 422/141; 208/134; 208/137

(58) Field of Classification Search ............... 585/323, 585/444, 316, 403, 441, 445, 600, 661, 315; 502/243; 422/139, 141; 208/134, 137
See application file for complete search history.

(56) References Cited

U.S. PATENT DOCUMENTS

| | | | |
|---|---|---|---|
| 4,830,728 A | | 5/1989 | Herbst et al. |
| 5,268,089 A | * | 12/1993 | Avidan et al. ............... 208/113 |
| 5,730,859 A | | 3/1998 | Johnson et al. |
| 5,770,045 A | * | 6/1998 | Gosling et al. ............. 208/137 |
| 5,994,258 A | * | 11/1999 | Buonomo et al. ........... 502/243 |
| 6,031,143 A | * | 2/2000 | Buonomo et al. ........... 585/323 |
| 6,841,712 B1 | * | 1/2005 | Iezzi et al. .................. 585/444 |
| 2003/0196933 A1 | | 10/2003 | Lomas et al. |

FOREIGN PATENT DOCUMENTS

| | | |
|---|---|---|
| EP | 0 529 661 A2 | 3/1993 |
| FR | 1.465.209 | 1/1967 |
| GB | 784414 | 10/1957 |
| GB | 1094855 | 12/1967 |
| WO | WO 02/096844 A1 | 12/2002 |
| WO | WO 03/053567 A2 | 7/2003 |

* cited by examiner

*Primary Examiner*—Glenn Caldarola
*Assistant Examiner*—Prem C. Singh
(74) *Attorney, Agent, or Firm*—Oblon, Spivak, McClelland, Maier & Neustadt, L.L.P.

(57) ABSTRACT

Process for production of styrene by dehydrogenation of ethylbenzene in a reactor system comprising a dehydrogenation reactor and a fast riser catalyst regenerator.

16 Claims, 1 Drawing Sheet

PROCESS FOR PRODUCTION OF STYRENE BY CATALYTIC GAS PHASE DEHYDROGENATION OF ETHYLBENZENE

The present invention relates to a reactor-regenerator device and its use in the production of styrene.

More specifically, the present invention relates to a reactor-regenerator device, comprising at least one reactor for catalytic dehydrogenation reactions of hydrocarbons and at least one regenerator of the catalyst of the fast riser type.

Even more specifically, the present invention relates to the use of said reactor-regenerator device in the dehydrogenation of ethylbenzene, optionally mixed with ethane. In particular, the present reactor-regenerator device can be used in the production of styrene.

The term "fast riser" as used in the present description and claims refers to a substantially tubular apparatus for chemical reactions which comprise a gaseous phase in close contact with a solid phase, wherein gas and solid particles move upwards in co-currently and the superficial velocity of the gas is higher than the terminal velocity of the solid particles and preferably higher than the double of said terminal velocity. Said reactor is particularly suitable for reactions in which a gaseous phase, for example a regenerating gas such as air, oxygen or oxygen-enriched air, is in contact with a solid in the form of particles, wherein the chemical reaction, for example the regeneration of an exhausted catalyst in particle form, is sufficiently fast as to take place in the low contact time typical of a "fast-riser type reactor".

Processes and equipment for effecting endothermic catalytic reactions, for example dehydrogenation, are known in literature, for example the "SOD Model IV" reactor cited by Zenz and Othmer in "Fluidization and Fluid Particles Systems" (Reinhold Publishing, 1960).

Processes are also known in literature, for the dehydrogenation of alkyl aromatic hydrocarbons, such as ethyl benzene, to give the corresponding vinyl aromatic derivative, such as styrene. U.S. Pat. No. 6,031,143, for example, describes a process for the contemporaneous production of styrene and ethylene, which comprises feeding ethyl benzene and ethane to a dehydrogenation reactor to produce ethylene and styrene by means of a catalytic system based on gallium oxide supported on alumina. The dehydrogenation reactor operates in combination with a regeneration reactor which continuously receives the exhausted catalyst which, after being regenerated and heated, is re-fed, still in continuous, to the dehydrogenation section.

The process summarized above envisages the use of a system consisting of a reactor and a fluid bed regenerator with a flow in countercurrent of gas and solid to effect both the dehydrogenation reaction and the regeneration phase of the catalyst. Fluid beds, however, have the disadvantage of requiring large-sized equipment and high quantities of catalyst, in proportion to the production capacity, to be able to operate appropriately. The superficial velocity of the gas in fluid bed reactors is, in fact, necessarily limited by the pneumatic carrying rate of the catalyst which is generally lower than 100-150 cm/sec.

An objective of the present invention is to provide a reactor-regenerator device still operating under fluid conditions but which allows catalytic dehydrogenation reactions to be carried out in gas phase without the drawbacks of the known art described above.

An object of the present invention therefore relates to a reactor-regenerator device for carrying out catalytic dehydrogenation reactions of ethylbenzene and/or ethane in gas phase comprising at least one reaction vessel suitable for dehydrogenation reactions in the presence of a solid catalyst in particle form and a regenerator of the catalyst directly connected to the reaction vessel consisting of a fast riser in which gas and solid move upwards co-currently and the superficial velocity of the gas is higher than the terminal velocity of the solid particles, preferably higher than the double of said terminal velocity. The superficial velocity of the gas is preferably lower than 30 m/sec in order to avoid erosion phenomena of the walls and minimize friction of the solid particles.

Figure 2:
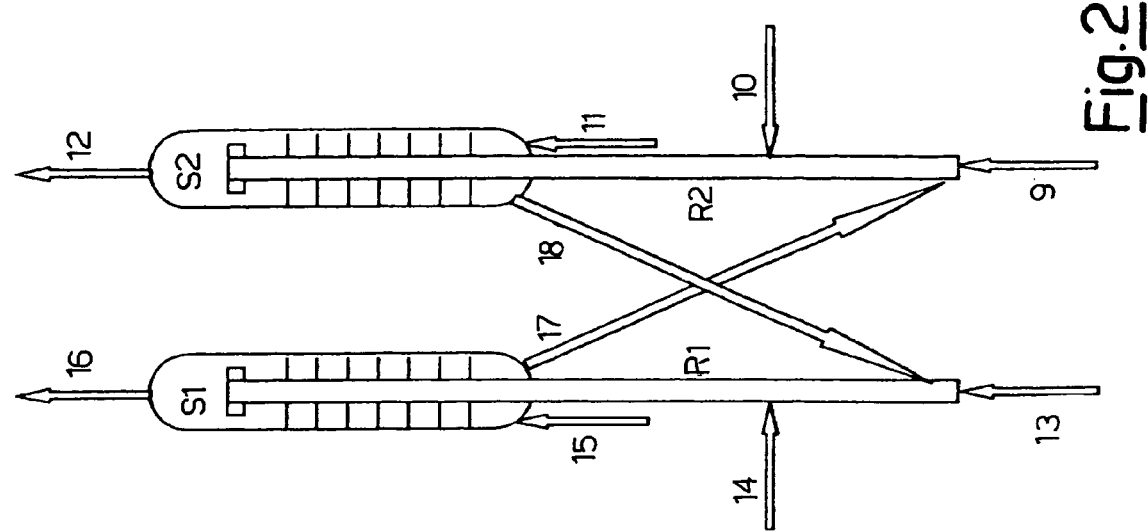
FIG. 2 shows a reactor regenerator device according to a second embodiment of the invention wherein the reactor is a reactor-riser.

According to the present invention, the reaction vessel can consist of one or more reactors for reactions which are carried out in a fluid bed, preferably a reactor in which the fresh or regenerated catalyst is charged from the top whereas the reagent in gas phase is fed at a position close to the bottom, through a specific distributor. Therefore, the gas, fed to the base of the reaction vessel, rises in countercurrent with respect to the catalyst which is descending, maintaining it under fluid bed conditions. Suitable internals, for example cylindrical grids or bars, capable of preventing the remixing of the gas and catalyst, are arranged inside each reaction vessel, so that the rising flow of gas and descending stream of solid inside each reaction vessel will be like a plug flow. The presence of a plug flow generally improves the conversion and selectivity of the dehydrogenation reaction.

Alternatively, if a sufficiently active catalyst is available, the reaction vessel can consist of at least one riser reactor operating under fluid conditions like those of the regenerator-riser. In the event of dehydrogenation reactions in which the reagent system comprises a mixture ethylbenzene/ethane, as in the case of U.S. Pat. No. 6,031,143, the reactor-riser can comprise at least two feeding points, one for each gaseous component, at different heights to enable each dehydrogenation reaction to be carried out under the most favourable operating conditions from a kinetic and thermodynamic point of view.

Alternatively, at least two reactor-risers arranged in parallel can be present, each fed with the respective reagent gas or with suitable mixtures of gases which can also comprise the effluent gas from another reactor-riser, with diluent functions. The catalyst flows in series along the various reactor-risers and is carried upwards co-currently by the reagent gas and then, due to gravity, downwards to the base of the subsequent reactor-riser.

According to a further embodiment of the present invention, the catalyst, coming directly from the regenerator-riser, can be fed in parallel to the various reactor-risers, optionally inserting some heat exchangers to cool part of the catalyst to the more convenient temperature for each reaction.

In each of the said reactor-risers, in which gas and solid move upwards co-currently, the superficial velocity of the gas is higher than the terminal velocity of the solid particles and preferably higher than the double of said terminal rate. The superficial velocity of the gas is preferably lower than 30 m/sec also for the reactor-risers, in order to avoid erosion phenomena of the walls and minimize friction of the solid particles.

The reaction vessel is directly connected to the regenerator-riser by means of a transfer line which allows the exhausted catalyst, which is collected on the bottom of the fluid bed reactor or which is recovered from the head of the reactor-riser, to be transferred to the regenerator, using a carrier gas which may be inert or the regenerating gas itself as carrier.

The regeneration gas is fed at a high temperature and is selected from air, oxygen, air or oxygen diluted with nitrogen, an inert gas, or concentrated with oxygen. The regeneration of the exhausted catalyst is effected exclusively with the regenerating gas, by the oxidation/combustion of the reaction residues, for example pitches or carbonaceous residues, such as coke, possibly deposited on the catalyst. Furthermore, as the catalyst is also heated in the regenerator-riser to bring it to the operating temperature present in the reaction vessel for the dehydrogenation reaction, inlet points of combustible gas are envisaged at the base of the regenerator-riser, also at different heights, to effect the heating of the regenerated catalyst by the catalytic combustion of said combustible gas such as methane or LPG or by the combustion of the hydrogen coming from the dehydrogenation reaction itself.

The reactor-regenerator device, object of the present invention, can also comprise a separation device, positioned at the outlet of the regenerator-riser, to recover the regenerated catalyst from the gas phase which entrains it. The separation device can consist of a cyclone separator on the bottom of which the regenerated catalyst is collected, which, stripped with an inert gas, for example nitrogen, to eliminate the possible entrained regenerating gas, is recycled to the reaction vessel using reagent gas, for example, as carrier. An apparatus suitable for separating the catalyst from the regenerating gas and which can be used, for this purpose, in the device object of the present invention, is described in U.S. Pat. No. 4,043,899.

A further object of the present invention relates to a process for carrying out the catalytic dehydrogenation reaction in gas phase of ethylbenzene and/or ethane which uses the reactor-regenerator device described above. In the case of a bi-component reagent gas, ethylbenzene+ethane, the reactor-regenerator system, object of the present invention, can be used in combination with the integrated process described in Italian patent 1,295,072, and its corresponding foreign extensions, as better defined in the claims.

More specifically, a further object of the present invention relates to a process for carrying out the catalytic dehydrogenation reaction of ethylbenzene and/or ethane in gas phase, which comprises:
i) Continuously feeding the reagent gas to a section comprising at least one reaction vessel, suited for carrying out the catalytic dehydrogenation reaction, containing a catalyst and operating under fluid conditions, for example fluid bed conditions;
ii) discharging the reaction product from the head of the vessel of step (i) to send it to the subsequent separation and recovery/recycling steps of the non-reacted components;
iii) continuously removing a stream of exhausted catalyst from the reaction vessel and, after optional stripping with inert gas in a specific apparatus, feeding it to a regeneration/heating section, comprising a regenerator-riser, using regenerating gas as carrier in co-current flow with the catalyst;
iv) continuously removing a stream of regenerated and heated catalyst from the head of the regenerator-riser and, after optional stripping with inert gas in a specific apparatus, feeding it to the dehydrogenation reactor using the reagent gas, or ethane in the case of a ethylbenzene/ethane mixture, as carrier.

In the case of the dehydrogenation of a bi-component reagent gas, such as ethane/ethyl benzene mixtures, it is possible to use a reactor-riser as reaction vessel, analogous to that described in international patent application WO 02/96844, or a pair of reactor-risers, each fed with one of the gases and maintained under the most favourable thermodynamic conditions for the reaction involved.

In the section where the dehydrogenation reaction takes place, the temperature ranges from 400 to 750° C. The pressure is atmospheric, or slightly higher, and the flow-rates of the reagents are regulated so as to obtain a GHSV (Gas Hourly Space Velocity) ranging from 100 to 1000 Nl/hl$_{cat}$, preferably from 150 to 450 Nl/hl$_{cat}$, and with residence times of the catalyst ranging from 5 to 30 minutes, preferably from 10 to 15 minutes, in the case of fluid bed reactors, or a GHSV higher than 2000 Nl/hl$_{cat}$ and residence times of the solid of less than 1 minute, in the case of reactor-risers.

The regeneration of the catalyst is generally carried out at a temperature higher than that of the dehydrogenation reaction, at atmospheric pressure, or slightly higher, at a GHSV higher than 2000 Nl/hl$_{cat}$, preferably higher than 3000 Nl/hl$_{cat}$, and with residence times of the catalyst of less than 1 minute and, preferably, less than 30 seconds. In particular, the regeneration temperature ranges from 500 to 750° C. and, preferably, the residence time is less than seconds.

Typical examples of catalysts which can be used in the dehydrogenation process object of the present invention are those based on gallium and manganese described in Italian patent application MI2001A 02709. These catalytic compositions comprise:
a) a carrier consisting of alumina in delta phase or in theta phase or a mixture of delta+theta phase, theta+alpha phase or delta+theta+alpha phase, modified with 0.08-5% by weight of silica, and having a surface area lower than 150 m$^2$/g, determined with the BET method;
b) 0.1-35% by weight, preferably 0.2-3.8% by weight of gallium expressed as $Ga_2O_3$;
c) 0.01-5% by weight, preferably 0.15-1.5%, of manganese expressed as $Mn_2O_3$;
d) 0-100 ppm by weight, preferably 5-90 ppm, of platinum;
e) 0.05-4% by weight, preferably 0.1-3%, of an oxide of an alkaline or alkaline-earth metal;

the percentages being calculated with respect to the total of the composition.

These catalysts can be prepared according to methods which comprise:
preparing one or more solutions of the components to be supported;
dispersing the solutions on the alumina carrier modified with silica;
drying the impregnated carrier; and
calcining the dried carrier at a temperature ranging from 500 to 900° C.;
optionally repeating the previous steps once or twice.

In the preparation of these catalysts, the modified alumina carrier is in the form of particles classified as belonging to group A according to Geldart (Gas Fluidization Technology, D. Geldart, John Wiley & Sons, 1986).

The dispersion of the catalyst components on the carrier can be carried out according to conventional techniques, such as impregnation, ion exchange, vapour deposition or surface adsorption. The incipient wetness impregnation technique is preferably used.

Catalysts based on gallium and manganese have also proved to be effective in the form of mechanical mixtures of the respective supported active metallic components. An example of a catalytic mechanical mixture is that in which the quantity of gallium (Ga$_2$O$_3$) ranges from 0.2 to 3.8% by weight, the quantity of manganese ranges from 0.15 to 1.5% by weight, the quantity of platinum ranges from 5 to 50 ppm by weight and the total quantity of alkaline or alkaline-earth metal oxide ranges from 0.1 to 3% by weight, the complement to 100 obviously being the supporting alumina in delta phase or theta phase or a mixture of delta+theta, theta+alpha or delta+theta+alpha phases, modified with 0.08-5% by weight of silica, and having a surface area lower than 150 m$^2$/g, determined with the BET method.

Further examples of particularly suitable catalysts are those described in international patent application PCT/EP 00/9196 based on iron and one or more promoters, selected from alkaline or alkaline-earth metals and lanthanides, on alumina in delta or theta phase or in a mixture of delta+theta, theta+alpha or delta+theta+alpha phases, modified with silica, and having a surface area preferably lower than 150 m$^2$/g, determined with the BET method. More specifically, these catalysts comprise:

- 1-60% by weight, preferably 1-20%, of iron oxide;
- 0.1-20% by weight, preferably 0.5-10%, of at least one alkaline or alkaline-earth metal oxide, for example potassium;
- 0-15% by weight, preferably 0.1-7%, of a second promoter selected from lanthanide oxides, for example cerium, lanthanum or praseodymium;
- the complement to 100 being alumina modified with 0.08-5% by weight of silica.

Other examples of catalysts are those based on gallium and platinum described in European patent 637,578. Catalysts based on gallium and platinum can be selected from those comprising:

- 0.1-34% by weight, preferably 0.2-3.8%, of Ga$_2$O$_3$;
- 1-99 ppm (by weight), preferably 3-80 ppm, of platinum;
- 0.05-5% by weight, preferably 0.1-3%, of an alkaline and/or alkaline-earth metal oxide, for example potassium;
- 0.08-3% by weight of silica; the complement to 100 being alumina in delta or theta phase or in a mixture of delta+theta, theta+alpha or delta+theta+alpha phases, with a surface area lower than 150 m$^2$/g, determined with the BET method.

Figure 1:
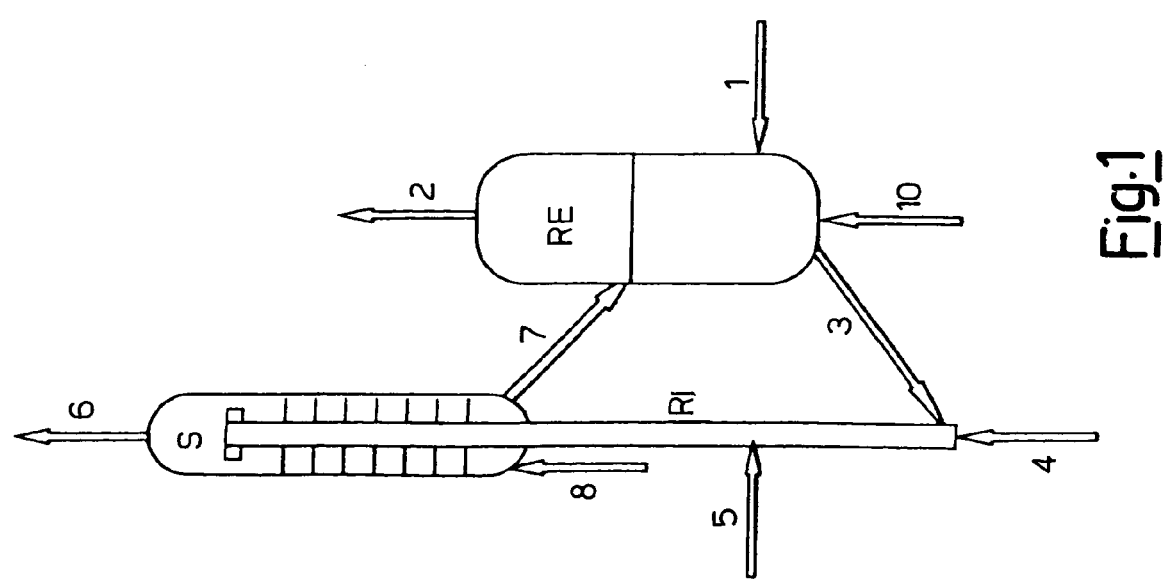
FIG. 1 shows a reactor regenerator device according to one embodiment of the invention wherein the reactor is a fluid bed vessel.

The reactor-regenerator device and the process for its use in catalytic dehydrogenation reactions in gas phase can be better understood by referring to the drawings of FIGS. 1 and 2 enclosed which represent an illustrative and non-limiting embodiment, and in which:

FIG. 1 represents a reactor-regenerator device wherein the reactor consists of a fluid bed vessel and the gaseous phase treated is bi-component (mixture of ethyl benzene and ethane);

FIG. 2 represents a reactor-regenerator device wherein the reactor consists of a reactor-riser and the gaseous phase is bi-component (mixture of ethyl benzene and ethane).

With reference to the figures, a first possible embodiment of the reactor-regenerator device, object of the present invention, envisages carrying out the reaction in a bubbling fluidized bed with a flow of gas and solid in countercurrent. In this case, the reagent mixture (1) is fed to the reactor (RE), where it rises in countercurrent with respect to the solid and partially reacts according to dehydrogenation reactions forming styrene and ethylene, before leaving the reactor by means of the effluent stream (2). The catalyst descends, due to gravity, and leaves the reactor from below by means of the stream (3) and, after being stripped from the interparticle gas by stream (10), consisting of nitrogen or another suitable gas, reaches the bottom of the fast riser regenerator (RI). Here, the catalyst is carried upwards by the stream (4) which, containing an adequate percentage of oxygen, is capable of burning both the surface coke produced during the reaction and also the stream of gaseous fuel (5), injected at a suitable height of the regenerator (RI). The co-current flow of gas and solid enters the separation unit, which can aptionally include a stripper (S) where, as a result of the reduced superficial velocity of the gas, the solid descends down-wards, whereas the stream of combusted gases (6) leaves the system from above. The solid descends in countercurrent with a stripping gas (8) and leaves the stripper by means of the stream (7) to be transferred to the upper part of the catalytic bed of the reactor (RE).

Alternatively (FIG. 2), with a suitable catalyst, a regenerator (R1) and a reactor (R2) both of the fast riser type can be coupled. In this case, the thermodynamically more stable hydrocarbon (ethane) is fed to the bottom of the reactor-riser (R2) by means of the stream (9), whereas the less stable hydrocarbon (ethylbenzene), is fed by means of stream (10) to a suitable height along the riser where, as a result of the dehydrogenation reaction of ethane which has cooled the catalyst, the temperature is such as to allow the dehydrogenation of ethyl benzene with a high selectivity to styrene. The mixture of reacted gas and catalyst enters the stripper (S2) where, in a disengagement zone, a stripping gas (11) flows upwards to leave the reactor by means of stream (12), whereas the solid descends towards the bottom in countercurrently with the stripping gas (11) and leaves the reactor to be carried (18) to the base of the regenerator-riser (R1). The regenerator operates as in the case described above, wherein the stream containing oxygen (13), fed at a high superficial velocity, causes the co-current upward flow of gas and solid, whereas the fuel gas (14) is fed to a suitable height along (R1). The mixture of solid and gas enters the stripper (S1), where there is a disengagement zone which allows the combusted gases to flow upwards, leaving (S1) by means of stream (16), whereas the solid descends in countercurrent with respect to the stream (15) of stripping gas, leaving the stripper at the bottom to be carried (17) to the bottom of the reactor-riser (R1). As an alternative to the intermediate feeding of the less stable hydrocarbon, it is possible to use a series of reactor-risers, in each of which the most suitable mixture of hydrocarbons is fed from below, whereas the solid flows from one to the other, starting from the reactor to which the thermodynamically more stable hydrocarbon is fed, and ending at the reactor-riser which is fed with the thermodynamically less stable hydrocarbon. The solid passes from this latter reactor to the fast riser reactor, after suitable stripping.

The invention claimed is:

1. A process for the catalytic dehydrogenation of ethylbenzene and/or ethane in gas phase, comprising:
  i) continuously feeding ethylbenzene and/or ethane to at least one reaction vessel, suited for carrying out a catalytic dehydrogenation reaction, comprising a catalyst and operating under fluid conditions;
  ii) discharging a reaction product from a head of the at least one reaction vessel, sending the reaction product to a subsequent separation, recovering and recycling of non-reacted components;
  iii) continuously removing a stream of exhausted catalyst from a lower portion of the at least one reaction vessel and, after stripping with an inert gas to remove interparticle gas, regenerating and heating the catalyst in a fast riser regenerator, using regenerating gas as carrier in equicurrent with the catalyst;
  iv) continuously removing a stream of regenerated and heated catalyst from the head of the fast riser regenerator and, after optional stripping with inert gas, feeding the regenerated and heated catalyst to an upper part of the dehydrogenation reactor using a reagent gas, or ethane in the case of ethylbenzene/ethane mixture, as carrier;

wherein a residence time of the catalyst in the fast-riser regenerator is less than 30 seconds.

2. The process according to claim 1, wherein the dehydrogenation reaction is carried out at a temperature ranging from 400 to 700° C., at about atmospheric pressure.

3. The process according to claim 1, wherein the regenerating and heating of the catalyst is carried out at a temperature higher than that of the dehydrogenation reaction, at about atmospheric pressure.

4. The process according to claim 3, wherein the regenerating and heating temperature ranges from 500 to 750° C.

5. The process according to claim 1, wherein the dehydrogenation catalyst comprises:
   a) a carrier consisting of alumina in delta phase or in theta phase or a mixture of delta+theta phase, theta+alpha phase or delta+theta+alpha phase, modified with 0.08-5% by weight of silica, and having a surface area lower than 150 m2/g, determined with the BET method;
   b) 0.1-35% by weight, of gallium expressed as $Ga_2O_3$;
   c) 0.01-5% by weight, of manganese expressed as Mn2O3;
   d) 0-100 ppm by weight, of platinum;
   e) 0.05-4% by weight, of an oxide of an alkali or alkaline-earth metal;
   the percentages being calculated with respect to the total of the composition.

6. The process according to claim 1, wherein the dehydrogenation catalyst is a mechanical mixture of the supported active metallic components wherein
   the quantity of gallium ($Ga_2O_3$) ranges from 0.2 to 3.8% by weight,
   the quantity of manganese ranges from 0.15 to 1.5% by weight,
   the quantity of platinum ranges from 5 to 50 ppm by weight and
   the total quantity of alkaline or alkaline-earth metal oxide ranges from 0.1 to 3% by weight,
   the complement to 100 being the supporting alumina in delta phase or theta phase or a mixture of delta+theta, theta+alpha or delta+theta+alpha phases, modified with 0.08-5% by weight of silica, and having a surface area lower than 150 m2/g, determined with the BET method.

7. The process according to claim 1, wherein the dehydrogenation catalyst comprises:
   a) 1-60% by weight, of iron oxide;
   b) 0.1-20% by weight, of at least one alkaline or alkaline-earth metal oxide;
   c) 0-15% by weight, of a second promoter selected from the group consisting of lanthanide oxides;
   d) the complement to 100 being alumina modified with 0.08-5% by weight of silica.

8. The process according to claim 1, wherein the dehydrogenation catalyst comprises:
   a) 0.1-34% by weight, of $Ga_2O_3$;
   b) 1-99 ppm (by weight), of platinum;
   c) 0.05-5% by weight, of an alkali and/or alkaline-earth metal oxide;
   d) 0.08-3% by weight of silica;
   the complement to 100 being alumina in delta or theta phase or in a mixture of delta+theta, theta+alpha or delta+theta+alpha phases, with a surface area lower than 150 m2/g, determined with the BET method.

9. The process according to claim 1, wherein ethylbenzene and ethane are fed to the at least one reaction vessel and the reaction product comprises styrene and ethylene.

10. The process according to claim 9, wherein the ethylene is recycled to an alkylation unit together with a stream of fresh benzene to prepare ethyl benzene.

11. The process according to claim 5, wherein the dehydrogenation catalyst comprises:
   a) a carrier consisting of alumina in delta phase or in theta phase or a mixture of delta+theta phase, theta+alpha phase or delta+theta+alpha phase, modified with 0.08-5% by weight of silica, and having a surface area lower than 150 m2/g, determined with the BET method;
   b) 0.2-3.8% by weight of gallium expressed as $Ga_2O_3$;
   c) 0.15 to 1.5% by weight of manganese expressed as Mn2O3;
   d) 5-90 ppm of platinum;
   e) 0.1-3% by weight of an oxide of an alkali or alkaline-earth metal;
   the percentages being calculated with respect to the total of the composition.

12. The process according to claim 7, wherein the dehydrogenation catalyst comprises:
   a) 1-20% by weight of iron oxide;
   b) 0.5-10% by weight of at least one alkali or alkaline-earth metal oxide;
   c) 0.1-7% by weight of a second promoter selected from the group consisting of lanthanide oxides;
   d) the complement to 100 being alumina modified with 0.08-5% by weight of silica.

13. The process according to claim 12, wherein the at least one alkali or alkaline-earth metal oxide is potassium oxide.

14. The process according to claim 12, wherein the second promoter is a lanthanide oxide selected from the group consisting of cerium, lanthanum and praseodymium.

15. The process according to claim 8, wherein the dehydrogenation catalyst comprises:
   a) 0.2-3% by weight of $Ga_2O_3$;
   b) 3-80 ppm by weight, of platinum;
   c) 0.1-3% by weight of an alkali and/or alkaline-earth metal oxide;
   d) 0.08-3% by weight of silica;
   the complement to 100 being alumina in delta or theta phase or in a mixture of delta+theta, theta+alpha or delta+theta+alpha phases, with a surface area lower than 150 $m^2$/g, determined with the BET method.

16. The process according to claim 15, wherein the at least one alkali or alkaline-earth metal oxide is potassium oxide.

* * * * *